US010307209B1

(12) United States Patent
Yu

(10) Patent No.: US 10,307,209 B1
(45) Date of Patent: Jun. 4, 2019

(54) BOUNDARY LOCALIZATION OF AN INTERNAL ORGAN OF A SUBJECT FOR PROVIDING ASSISTANCE DURING SURGERY

(71) Applicant: SONY CORPORATION, Tokyo (JP)

(72) Inventor: Liangyin Yu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/057,044

(22) Filed: Aug. 7, 2018

(51) Int. Cl.
| | |
|---|---|
| *A61B 34/10* | (2016.01) |
| *G06T 7/11* | (2017.01) |
| *G06T 7/13* | (2017.01) |
| *G06T 7/38* | (2017.01) |
| *A61B 1/313* | (2006.01) |
| *G06T 7/73* | (2017.01) |
| *A61B 34/20* | (2016.01) |

(52) U.S. Cl.
CPC .......... *A61B 34/10* (2016.02); *A61B 1/3132* (2013.01); *A61B 34/20* (2016.02); *G06T 7/11* (2017.01); *G06T 7/13* (2017.01); *G06T 7/38* (2017.01); *G06T 7/74* (2017.01); *A61B 2034/107* (2016.02); *A61B 2034/2055* (2016.02); *A61B 2034/2065* (2016.02); *G06T 2207/10016* (2013.01); *G06T 2207/10068* (2013.01); *G06T 2207/20081* (2013.01); *G06T 2207/30004* (2013.01)

(58) Field of Classification Search
CPC ......... A61B 34/20; A61B 1/3132; G06T 7/74; G06T 7/38; G06T 7/11; G06T 7/13
See application file for complete search history.

(56) References Cited

U.S. PATENT DOCUMENTS

| 8,768,022 | B2 | 7/2014 | Miga et al. | |
|---|---|---|---|---|
| 9,129,422 | B2 | 9/2015 | Mountney et al. | |
| 2007/0081712 | A1* | 4/2007 | Huang | G06T 7/33 382/128 |

(Continued)

FOREIGN PATENT DOCUMENTS

WO  2016/170372 A1  10/2016

OTHER PUBLICATIONS

Zhu, et al., "Computerized Medical Imaging and Graphics", Computerized Medical Imaging and Graphics, Elsevier, 2012, 10 pages.

(Continued)

*Primary Examiner* — Edward Park
(74) *Attorney, Agent, or Firm* — Chip Law Group

(57) ABSTRACT

A surgical assistive apparatus and method to provide assistance during surgery, includes an organ boundary localization circuit that selects a test video frame from a captured sequence of video frames and derives a first global region boundary of an internal organ of interest in the selected test video frame by integration of an appearance likelihood result, a global segmentation result, and a global edge detection result associated with the internal organ of interest. A plurality of local region boundaries are determined for a plurality of local sub regions of the internal organ of interest and a second global region boundary is generated for the internal organ of interest based on the determined plurality of local region boundaries and the first global region boundary. The internal organ of interest is localized based on the generated second global region boundary.

19 Claims, 8 Drawing Sheets

(56) References Cited

U.S. PATENT DOCUMENTS

| | | | | |
|---|---|---|---|---|
| 2007/0167699 A1* | 7/2007 | Lathuiliere | ............... | G06T 7/12 600/407 |
| 2012/0257805 A1* | 10/2012 | Gloger | ............... | G01R 33/5608 382/128 |
| 2016/0140725 A1* | 5/2016 | Bergner | .................. | G06T 5/002 382/173 |

OTHER PUBLICATIONS

Collins, et al., "Robust, Real-time, Dense and Deformable 3D Organ Tracking in Laparoscopic Videos", 08 pages.

* cited by examiner

BOUNDARY LOCALIZATION OF AN INTERNAL ORGAN OF A SUBJECT FOR PROVIDING ASSISTANCE DURING SURGERY

CROSS-REFERENCE TO RELATED APPLICATIONS/INCORPORATION BY REFERENCE

None.

FIELD

Various embodiments of the disclosure relate to a surgical assistive device. More specifically, various embodiments of the disclosure relate to a surgical assistive device and method for a boundary localization of an internal organ of a subject for providing assistance during surgery.

BACKGROUND

Advancements in the field of medical imaging techniques and associated sensors and/or devices have facilitated use of display devices that help visualize interior of a human or animal body during clinical analysis and surgical procedures. The visualization is usually done by a surgeon who physically inserts an instrument embedded with a miniaturized camera inside the body of a subject, via an incision or an opening in the body of the subject. For example, a surgeon may insert a laparoscope within the body of a subject to visualize different internal organs, such as liver, spleen, kidney, and the like, on a screen during surgery or a clinical examination.

The foremost reason to visualize such internal organs is associated with an estimation of the locations of specific organs of interest within the body of the subject within a region associated with the incision in the body. In practice, the visibility of such specific internal organs on the display screen may be affected by a presence of blood, gases, tissues that may lie in a field-of-view (FOV) of the instrument. The view of the internal organ may be further blocked by tumor growths on the same internal organ or other neighboring organs and the presence of such abnormal cell growth may change the appearance of the internal organ. Additionally, certain patients' may exhibit variations in anatomical features of specific internal organs, such as variations in position, size, shape, and appearance of the internal organ, which may be caused by an infection or a disease. A mere assumption of the location and region of the internal organ from a given visual on the screen during surgery may risk the life of the subject. The accuracy of such assumptions may further depend upon an experience level of the surgeon and therefore, a precise and improved systems may be required to provide a concrete support and assistance during surgery.

Further limitations and disadvantages of conventional and traditional approaches will become apparent to one skilled in the art, through comparison of described systems with some aspects of the present disclosure, as set forth in the remainder of the present application and with reference to the drawings.

SUMMARY

A surgical assistive device and method are provided for boundary localization of an internal organ of a subject for providing assistance in a surgery, as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Certain embodiments of the disclosure may be found in a surgical assistive device and method for boundary localization of an internal organ of a subject for providing assistance in a surgery. Various embodiments of the disclosure may provide a surgical assistive device. The surgical assistive device may include a surgical image-capture device and an organ boundary localization circuit communicatively coupled to the surgical image-capture device. The surgical image-capture device may be configured to capture a sequence of video frames of one or more internal organs of a subject. The sequence of video frames of the one or more internal organs of the subject may be captured based on insertion of the surgical image-capture device in the body of the subject. In some embodiments, the internal organ may be an abdominal organ, for example, liver, pancreas, stomach, and the like.

Various embodiments of the disclosure provide a surgical assistive device that may precisely generate a boundary of an entire internal organ of interest of the subject rather than for some portion of the internal organ of interest. The boundary of the internal organ of interest generated by the surgical assistive device may help a surgeon in image-guided surgery to track the internal organ of interest of the subject. The boundary of the internal organ of interest generated by the surgical assistive device may further facilitate a registration of modified intra-operative images for the internal organ of interest with pre-operative imaging data obtained from a mode different from the surgical image-capture device. The modified intra-operative images may correspond to the generated boundary of the internal organ of interest overlapped on a localized internal organ of interest in a test video frame and subsequent test video frames that are a part of the captured sequence of video frames received as a continuous video feed.

Figure 1:
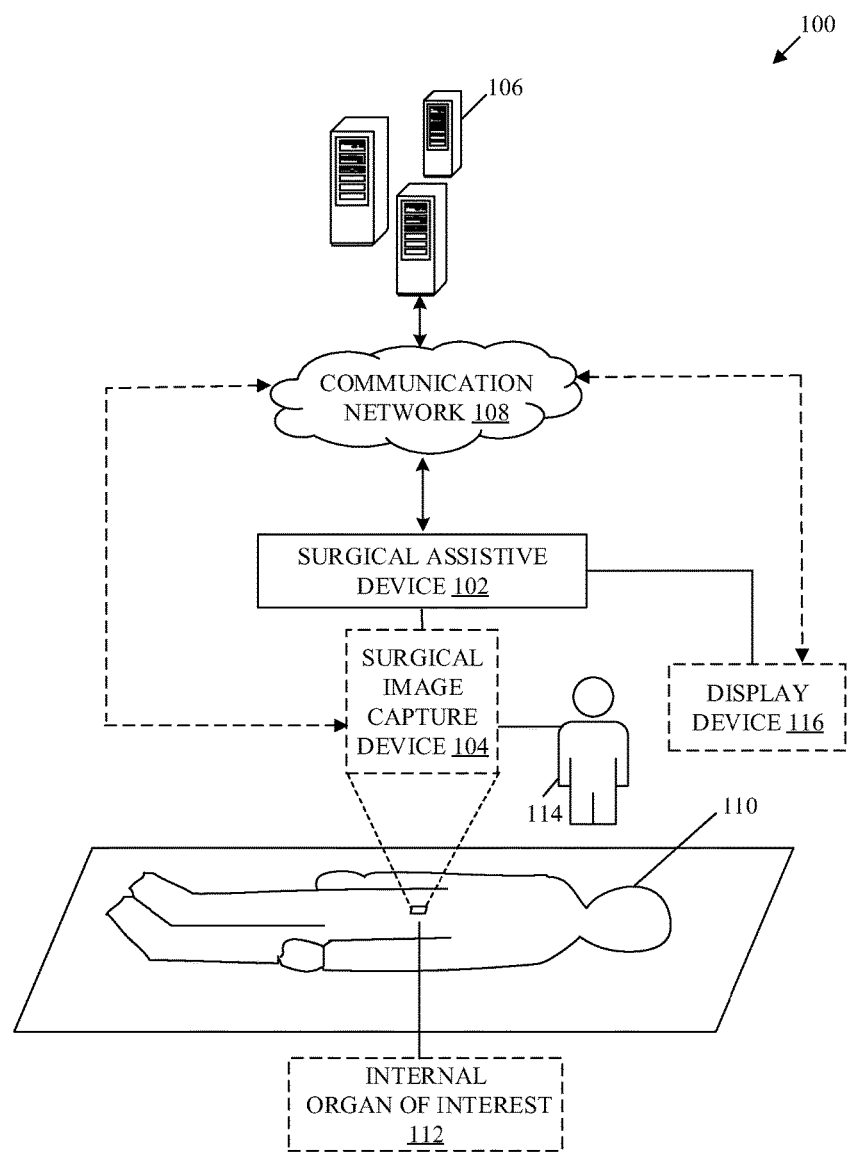
FIG. 1 is a diagram that illustrates a network environment for providing assistance in a surgical procedure that involves localization of a boundary of an internal organ of a subject, in accordance with an embodiment of the disclosure.

FIG. 1 is a diagram that illustrates a network environment for boundary localization of an internal organ of a subject for providing assistance in a surgery, in accordance with an embodiment of the disclosure. With reference to FIG. 1, there is shown a network environment 100 that may include a surgical assistive device 102, a surgical image-capture device 104, a medical data server 106, and a communication network 108. There is further shown one or more subjects, such as a human subject 110, an internal organ of interest 112 of the human subject 110, and a surgeon 114. The surgical assistive device 102 may be communicatively coupled to the surgical image-capture device 104, and the medical data server 106, via the communication network 108. In some embodiments, the surgical assistive device 102 may include a display device 116. In some embodiments, the surgical assistive device 102 may be communicatively coupled to the display device 116.

The surgical assistive device 102 may comprise suitable logic, circuitry, interfaces, and/or code that may be configured to generate a boundary for an internal organ, such as the internal organ of interest 112, of the human subject 110 for providing assistance in a surgery. The surgical assistive device 102 may provide a real-time or near real-time assistance to the surgeon 114 in a surgery by the localization of internal organ of interest 112 of the human subject 110 with the generation of the boundary of the internal organ of interest 112. Examples of the surgical assistive device 102 may include, but are not limited to, a computer-assisted surgical system or a robot-assisted surgical system, a medical device, an electronic surgical instrument, a display device, and/or a computing device.

In accordance with an embodiment, the surgical assistive device 102 may further include a surgical image-capture device 104. The surgical image-capture device 104 may capture one or more video frames of the internal organ of interest 112 of the human subject 110 when a surgery or diagnostic procedure is performed on the internal organ of interest 112. Alternatively, the surgical assistive device 102 may be communicatively coupled to the surgical image-capture device 104, via the communication network 108. Examples of the surgical image-capture device 104 may include, but are not limited to, an endoscopic/laparoscopic camera, a medical resonance imaging (MRI) device, a computer tomography (CT) scanning device, a minimally invasive medical imaging device, and/or a minimal incision medical imaging device.

The medical data server 106 may comprise suitable logic, circuitry, and interfaces that may be configured to store one or more datasets of training images, where each dataset may include a plurality of training images related to an appearance likelihood result of the internal organ of interest 112. The training images in the one or more datasets may include the imaging data of the internal organ of interest 112 of different human subjects. In accordance with an embodiment, the medical data server 106 may be configured to provide pre-stored versions of the one or more datasets to the surgical assistive device 102, via the communication network 108. In accordance with an embodiment, the surgical assistive device 102 may directly receive the one or more datasets from an external database (not shown in the figure) that may be different from the medical data server 106. In accordance with an embodiment, both the medical data server 106 and the surgical assistive device 102 may be integrated as a standalone computer-assisted surgical system. The medical data server 106 may be implemented as a plurality of cloud-based resources by several technologies that are well known to those skilled in the art. Examples of the medical data server 106 may include, but are not limited to, a file server, an application medical data server, and a web medical data server.

A person of ordinary skill in the art will understand that the scope of the disclosure is not limited to an implementation of the medical data server 106 and the surgical assistive device 102 as separate entities. In accordance with an embodiment, the functionalities of the medical data server 106 may be implemented by the surgical assistive device 102, without departure from the scope of the disclosure.

The communication network 108 may include a medium through which the surgical assistive device 102, the surgical image-capture device 104, and/or the medical data server 106 may communicate with each other. The communication network 108 may be a wired or wireless communication network. Examples of the communication network 108 may include, but are not limited to, a Local Area Network (LAN), a Wireless Local Area Network (WLAN), a cloud network, a Long Term Evolution (LTE) network, a plain old telephone service (POTS), a Metropolitan Area Network (MAN), and/or the Internet. Various devices in the network environment 100 may be configured to connect to the communication network 108, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

In accordance with an embodiment, the internal organ of interest 112 may be an internal organ of a subject, such as the human subject 110. The internal organ of interest 112 may correspond to an abdominal organ. The abdominal organ may include a liver, a left kidney, a right kidney, a spleen, a pancreas and/or the like. The internal organ of interest 112 may include infected abdominal organ, diseased abdominal organ and/or the abdominal organs with cyst, tumor or other abnormal growth.

A person of ordinary skill in the art will understand that the scope of the disclosure is not limited to implementation of the disclosed surgical assistive device 102 and method to assist in a surgery of the internal organ of interest 112 of the human subject 110, as shown. In accordance with an embodiment, the disclosed surgical assistive device 102 and method may be used to assist in a surgery of the internal organ of interest 112 of an animal subject. Further, the disclosed surgical assistive device 102 and method may also be useful to provide assistance in a surgery of anatomical portions or regions other than the abdominal organs, as discussed above.

The display device 116 may comprise suitable logic, circuitry, interfaces, and/or code that may be configured to display a sequence of video frames to a user, such as the surgeon 114. In accordance with an embodiment, the display device 116 may display a test video frame from the sequence of video frames, in real time or near-real time, while the surgical or diagnostic procedure is performed on the internal organ of interest 112 of the human subject 110. The display device 116 may be further configured to display the boundary localization of the internal organ of interest 112 of the human subject 110 that may be detected in the test video frame by the medical data server 106. Examples of the display device 116 may include, but are not limited to, a smartphone, a camera, a tablet computer, a laptop, a wearable electronic device, a television, an Internet Protocol Television (IPTV), and/or a Personal Digital Assistant (PDA) device.

A person of ordinary skill in the art will understand that in accordance with an embodiment, the display device 116 may be integrated with the surgical assistive device 102. Alternatively, the display device 116 may be communicatively coupled to the surgical assistive device 102. A user, such as the surgeon 114, of the display device 116 may control the surgical assistive device 102, with visual support, instructions, and/or guidance from a user-interface of the display device 116.

In operation, a user (e.g., the surgeon 114) may utilize the surgical assistive device 102 to perform a surgical or diagnostic procedure on the internal organ of interest 112 of the human subject 110. Examples of the surgical or diagnostic procedure may include, but are not limited to, a minimally invasive surgery/diagnosis procedure, a minimal incision surgery/diagnosis procedure, a laparoscopic procedure, and/or an endoscopic procedure. In accordance with the surgical procedure, the surgeon 114 may insert the surgical image-capture device 104 in a specific region, such as an abdominal region, of the body of the human subject 110. The surgical image-capture device 104 may be attached to an instrument, such as a laparoscope and may further include an image sensor (not shown) to capture a sequence of video frames within the body of the human subject 110. For example, the surgical image-capture device 104 may be attached to one end of the laparoscope. The laparoscope that may carry the surgical image-capture device 104 may be further inserted through an incision in the body of the human subject 110.

For example, the surgeon 114 may want to find a boundary of an entire internal organ of interest 112 inside the body of the human subject 110 for computer assisted navigation of the laparoscope within the body of the human subject 110. Such computer assisted navigation may further facilitate the surgeon 114 in image-guided surgery to track the internal organ of interest 112 of the subject. In accordance with an embodiment, a boundary of the internal organ of interest 112 generated by the surgical assistive device 102 may help in registration of modified intra-operative images for the internal organ of interest 112 with pre-operative imaging data obtained from a mode different from the surgical image-capture device 104. The modified intra-operative images may correspond to the generated boundary of the internal organ of interest 112 overlapped on a localized internal organ of interest 112 in a test video frame and subsequent test video frames that may be a part of the captured sequence of video frames, received as a continuous video feed.

In accordance with an embodiment, the internal organ of interest 112 may be an abdominal organ, for example, a liver, which the surgeon 114 may want to precisely locate in a laparoscopic surgery. In some embodiments, the internal organ of interest 112 may include, but are not limited to lungs, a pancreas, a spleen, a pair of kidneys, and the like. In certain scenarios, the internal organ that has to be examined or resected may not be clearly visible to the surgeon 114 because of the presence of blood, gases, tissues that may lie in a field-of-view of the surgical image-capture device 104. In some cases, the field-of-view of the internal organ of interest 112 may be blocked by tumor growth on the same organ or neighboring organs. The presence of such abnormal cell growth may change the appearance of the internal organ of interest 112 that is to be examined or resected by the surgeon 114.

Certain patients may have different anatomical structures that may cause variations in the position, size, shape, and appearance of the internal organ associated with such anatomical structures, for example, an abdominal organ. In certain other scenarios, the appearance of the organ of interest 112 of the human subject 110 may be different from the normal appearance due to an infection or a disease. Thus, a location of the internal organ of interest 112 may be imperfectly assumed within body of the subject 110 as a result of the inherent anatomical structure variations and complexity of the internal organs during surgery. Such imperfect assumptions for the location of the internal organ may further pose a negative impact on accuracy and proficiency of the surgeon 114 while performing a surgery and may further put safety of the subject 110 in jeopardy. Therefore, the surgical assistive device 102 may be configured to assist the surgeon 114 in way that appearance complexities and location-based bias may be reduced, and a safe, accurate, and quick assistance may be provided during surgery. Such aforementioned issues may be solved based on a robust identification of a boundary of the internal organ of interest 112 within the captured sequence of the frames, to further assist the surgeon 114 at real time surgical procedure. Such boundary estimation may mitigate bias of the surgeon 114 generated based on abnormal appearance, growth, variations in anatomical structure, and other factors.

In accordance with an embodiment, the surgical image-capture device 104 may be configured to capture a sequence of video frames (e.g., a video) of the one or more internal organs of the human subject 110, based on insertion of the surgical image-capture device 104 in the body of the human subject 110, via an incision or a specific passage within the body of the subject 110. The captured sequence of video frames may include a portion or an entire view of the one or more internal organs of the human subject 110.

In accordance with an embodiment, the surgical assistive device 102 may be configured to receive the captured sequence of video frames from the surgical image-capture device 104. As the captured sequence of video frames may include a portion or an entire view of different internal organs of the human subject 110, certain images may be selected from the captured sequence of video frames for further processing to avoid selection of unwanted image frames. For example, selected images may capture a view of internal organs from different viewing angles. The unwanted image frames may have a view where the internal organ of interest 112 may be absent or a quality score of the view may be less than a threshold quality as a result of presence of other anatomical portions of the human subject 110.

The surgical assistive device 102 may be further configured to select a test video frame from the received sequence of video frames. The selection of the test video frame may be done based on an area occupied by the internal organ of interest 112 in the test video frame. The test video frame may be selected when the area occupied by the internal organ of interest 112 in the test video frame may be greater than a threshold area. In accordance with an embodiment, the surgical assistive device 102 may be further configured to receive a dataset of the plurality of training images related to an appearance likelihood result from the medical data server 106. The surgical assistive device 102 may be further configured to utilize the received plurality of training images to compute an appearance likelihood of the internal organ of interest 112 in the test video frame. The computed appearance likelihood may generate an appearance likelihood result of the internal organ of interest 112 in the test video frame. In accordance with an embodiment, the appearance likelihood result may be computed based on further computations of a color likelihood and a texture likelihood of the internal organ of interest 112 in the test video frame.

In accordance with an embodiment, the surgical assistive device 102 may be further configured to compute the color likelihood of the internal organ of interest 112 in the test video frame. The computation of the color likelihood may be done based on a comparison of a color component of the portion of the test video frame with a color component in the plurality of training images. The color component may correspond to a Red, Green, and Blue (RGB) color model. The surgical assistive device 102 may be further configured to compute the texture likelihood of the internal organ of interest 112 in the test video frame. The computation of the texture likelihood of the internal organ of interest 112 in the test video frame may be done based on a comparison of the texture component of the test video frame with the texture component in the plurality of training images. The color likelihood and the texture likelihood may be computed independent of each other to derive the appearance likelihood result of the internal organ of interest 112 in the test video frame.

In accordance with an embodiment, the surgical assistive device 102 may be further configured to globally segment the test video frame to a plurality of regions to obtain a global segmentation result. In accordance with an embodiment, the surgical assistive device 102 may be further configured to assign a different color to each of the plurality of regions. In accordance with an embodiment, the surgical assistive device 102 may be further configured to detect edges of the plurality of regions in the global segmentation result. A global edge detection result may be further generated based on the detection of the edges of the plurality of regions in the global segmentation result. In accordance with an embodiment, the surgical assistive device 102 may be configured to recolor the plurality of regions in the global segmentation result of the test video frame based on the four-color theorem. Alternatively stated, different regions may be recolored with four different colors (or more colors) to maximize a contrast between adjacent regions of the plurality of regions and obtain distinct edges in the global edge detection result.

In accordance with an embodiment, the surgical assistive device 102 may be configured to derive a first global region boundary of the internal organ of interest 112. The first global region boundary may be derived based on integration of the appearance likelihood result, the global segmentation result, and the global edge detection result associated with the internal organ of interest 112 in the selected test video frame. In accordance with an embodiment, the surgical assistive device 102 may be further configured to select a plurality of local sub regions to determine a plurality of local boundaries based on the generated first global region boundary of the internal organ of interest 112. In accordance with an embodiment, the surgical assistive device 102 may be configured to locally segment the plurality of local sub regions of the internal organ of interest 112 in the selected test video frame. A local segmentation result may be further generated based on the local segmentation of the plurality of local sub regions of the internal organ of interest 112.

In accordance with an embodiment, the surgical assistive device 102 may be further configured to dilate the generated edges of the plurality of local sub regions. The dilation of the edges may be done based on the first global region boundary of the internal organ of interest 112 and the local segmentation result. The generated edges of the plurality of local sub regions may include a first type of edges and a second type of edges. The first type of edges may include edges above a threshold value and the second type of edges may include edges below the threshold value. The first type of edges may be relatively more continuous as compared to the second type of edges that are discontinuous. Therefore, the first type of edges may be referred as strong edges and the second type of edges may be referred as weak edges.

The surgical assistive device 102 may be further configured to retain the first type of edges from the generated edges of the plurality of local sub regions of the internal organ of interest 112 based on a masking operation on the second type of edges. The first type of edges may be further enhanced based on the dilated edges of the plurality of local sub regions. The enhanced first type of edges may exhibit a specific sharpness. However, such enhanced edges may lack sufficient consistency and continuity to be considered as a determinate boundary for the internal organ of interest 112. Therefore, the surgical assistive device 102 may be further configured to interpolate the retained first type of edges of each local sub region of the plurality of local sub regions of the internal organ of interest 112 by a single curve. The surgical assistive device 102 may be further configured to generate a single color space fitting boundary on the interpolated single curve for each local sub region of the plurality of local sub regions. A local boundary may be further determined from the generated single color space fitting boundary for each local sub region of the plurality of local sub regions in the test video frame.

The surgical assistive device 102 may be further configured to determine a plurality of local region boundaries for the plurality of local sub regions of the internal organ of interest 112 in the selected test video frame. The determination of the local region boundaries may be done based on the local segmentation result and the local edge detection result of each of the plurality of local sub regions of the internal organ of interest 112. The plurality of local region boundaries may be determined with guidance from the derived first global region boundary of the internal organ of interest 112. The plurality of local regions boundary may be least affected by global variations in region boundary of the internal organ of interest 112. Therefore, the plurality of local region boundaries may be integrated based on guidance from the derived first global region boundary of the internal organ of interest 112. Thereafter, the surgical assistive device 102 may be configured to generate a second global region boundary for the internal organ of interest 112 in the test video frame of the captured sequence of video frames. The second global region boundary may trace a boundary of the internal organ of interest 112 that may exhibit a minimum deviation from an actual boundary of the internal organ of interest 112. The generation of such second global region boundary may be done based on the determined plurality of local region boundaries and the first global region boundary.

In accordance with an embodiment, the surgical assistive device 102 may be further configured to register modified intra-operative images for the internal organ of interest 112 with pre-operative imaging data obtained from a mode different from the surgical image-capture device 104. The modified intra-operative images may correspond to the generated second global region boundary overlapped on the localized internal organ of interest 112 in the test video frame and subsequent test video frames of a continuous video feed.

In accordance with an embodiment, the surgical assistive device 102 may be further configured to localize the internal organ of interest 112 within the body of the subject in the surgery. The localization of the internal organ of interest 112 may be done based on the generated second global region boundary for the internal organ of interest 112. Additionally, the surgical assistive device 102 may be further configured to overlap the generated second global region boundary for the internal organ of interest 112 at a contour of the localized internal organ of interest 112 in the test video frame and different test video frames of a continuous video feed captured via the surgical image-capture device 104.

The surgical assistive device 102 may be further configured to display, at the display device 116, the generated second global region boundary in the modified sequence of video frames as a continuous feed captured by the surgical image-capture device 104, in real time or near-real time. In accordance with an embodiment, the surgical assistive device 102 may be further configured to generate instructions to enable navigation of the surgical image-capture device 104 and a surgical instrument within the body of the subject to reach to the localized internal organ of interest 112 for a precision image-guided surgery of the localized internal organ of interest 112.

Figure 2:
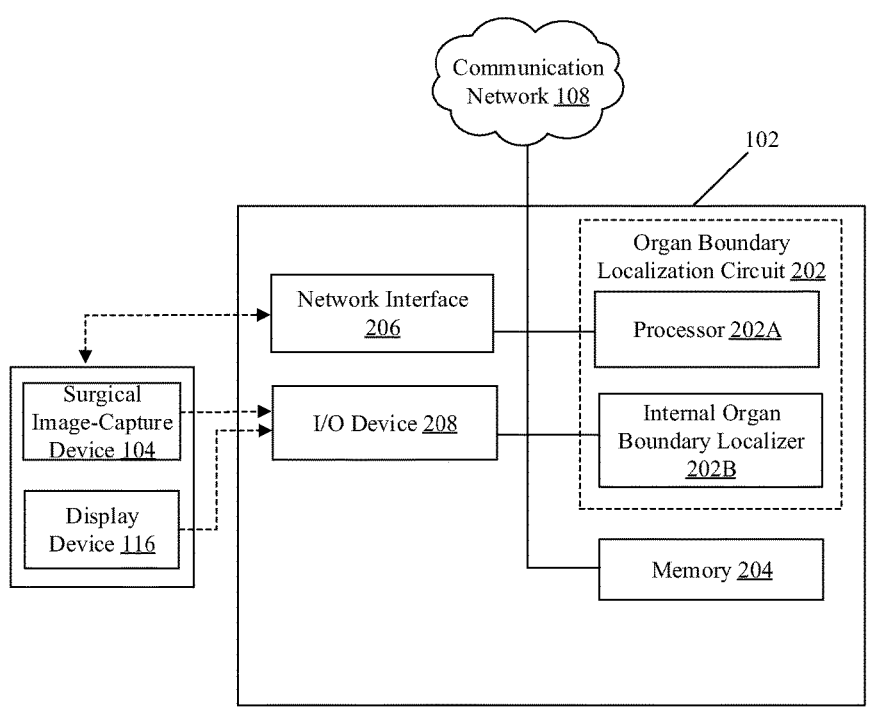
FIG. 2 illustrates a block diagram of an exemplary surgical assistive device that localizes a boundary of an internal organ of a subject for providing assistance in a surgery, in accordance with an embodiment of the disclosure.

FIG. 2 illustrates a block diagram of an exemplary surgical assistive device for boundary localization of an internal organ of a subject for providing assistance during surgery, in accordance with an embodiment of the disclosure. FIG. 2 is explained in conjunction with elements from FIG. 1. With reference to FIG. 2, there is shown the surgical assistive device 102. The surgical assistive device 102 may include one or more circuits, such as an organ boundary localization circuit 202, a memory 204, a network interface 206, one or more input/output (I/O) devices, such as an I/O device 208. The organ boundary localization circuit 202 may include a processor 202A, and an internal organ boundary localizer 202B.

The I/O device 208 may be communicatively coupled to the surgical image-capture device 104 and the display device 116, via the communication network 108. Alternatively, the I/O device 208 may be directly coupled to the surgical image-capture device 104 and the display device 116 through dedicated buses and/or channels. The organ boundary localization circuit 202 may be communicatively coupled to the memory 204, the network interface 206, and the I/O device 208. The network interface 206 may communicate with the one or more medical data server 106s, such as the medical data server 106, via the communication network 108 under the control of the organ boundary localization circuit 202.

The organ boundary localization circuit 202 may comprise suitable logic, circuitry, interfaces, and/or code that may be configured to localize a boundary of the internal organ of interest 112 of the human subject 110. Such boundary localization may be done based on implementation of different image processing techniques by different components of the organ boundary localization circuit 202. The organ boundary localization circuit 202 may be implemented based on a number of processor technologies known in the art. Examples of the organ boundary localization circuit 202 may be an X86-based processor, X86-64-based processor, a Reduced Instruction Set Computing (RISC) processor, an Application-Specific Integrated Circuit (ASIC) processor, a Complex Instruction Set Computing (CISC) processor, a central processing unit (CPU), an Explicitly Parallel Instruction Computing (EPIC) processor, a Very Long Instruction Word (VLIW) processor, and/or other processors or circuits.

The processor 202A may comprise suitable logic, circuitry, and interfaces that may be configured to execute a set of instructions stored in the memory 204. Examples of the processor 202A may be an x86-based processor, x86-64-based processor, an ASIC processor, a CPU, an EPIC processor, a VLIW processor, and/or other processors or circuits.

The internal organ boundary localizer 202B may comprise suitable logic, circuitry, and interfaces that may be configured to localize the internal organ of interest 112 within the body of the human subject 110 in the surgery, based on a global region boundary generated for the internal organ of interest 112. In accordance with an embodiment, the second global region boundary may be generated based on a determined plurality of local region boundaries and a first global region boundary for the internal organ of interest 112 in the test video frame of the captured sequence of video frames. The internal organ boundary localizer 202B may be implemented based on a number of processor technologies known in the art. Examples of the internal organ boundary localizer 202B may be an x86-based processor, x86-64-based processor, a RISC processor, an ASIC processor, a CISC processor, a CPU, an EPIC processor, a VLIW processor, and/or other processors or circuits.

The memory 204 may comprise suitable logic, circuitry, and/or interfaces that may be configured to store a machine code and/or a set of instructions executable by the organ boundary localization circuit 202. The memory 204 may be configured to store dataset of a plurality of training images related to appearance likelihood result corresponding to the internal organ of interest 112. The dataset may be retrieved from the medical data server 106 and stored at the memory 204. The memory 204 may be further configured to store a sequence of video frames captured by the surgical image-capture device 104. The memory 204 may be further configured to store operating systems and associated applications. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The network interface 206 may comprise suitable logic, circuitry, and interfaces that may be configured to communicate with the surgical image-capture device 104, the medical data server 106, and/or the display device 116, via the communication network 108 (as shown in FIG. 1). The network interface 206 may implement known technologies to support wired or wireless communication of the surgical assistive device 102 with the communication network 108. The network interface 206 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The I/O device 208 may comprise suitable logic, circuitry, and interfaces that may be configured to receive an input from and provide an output to a user based on the received input from the user. The I/O device 208 may receive an input from the surgical image-capture device 104 and provide an output to the display device 116 that may include visualizations and other data to render interactivity and/or other services to the user. Such visualizations and other data may be rendered with support from the surgical assistive device 102. Examples of the input devices may include, but are not limited to, the surgical image-capture device 104, a touch screen, a camera, a keyboard, a mouse, a joystick, a microphone, a motion sensor, a light sensor, and/or a docking station. Examples of the output devices may include, but are not limited to, the display device 116, a projector screen, and/or a speaker. Various operations of the different components of the surgical assistive device 102, may be further understood in details, for example, from FIGS. 3A to 3C, 4A, 4B, and 4C.

Figure 3A:
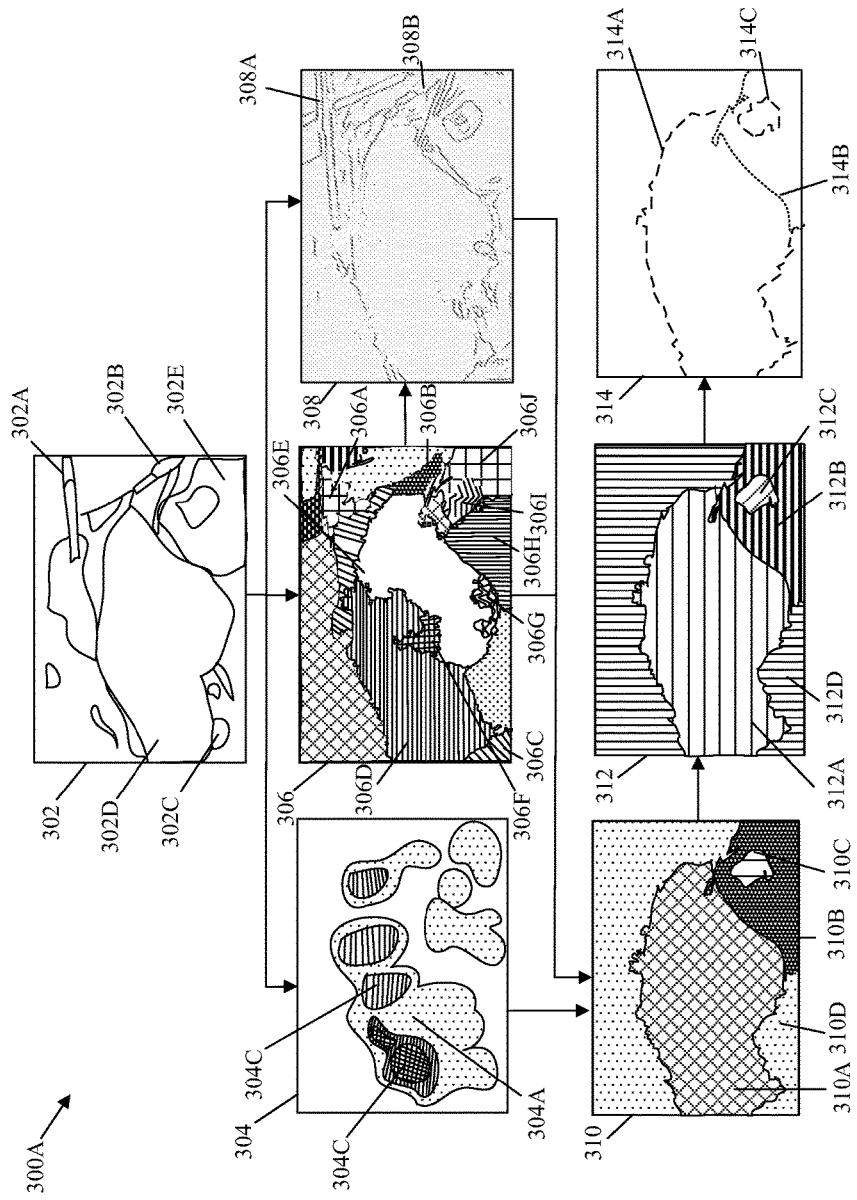
FIG. 3A illustrates a scenario to depict a processing pipeline for derivation of a first global region boundary for boundary localization of an abdominal organ of a subject, in accordance with an embodiment of the disclosure.

FIG. 3A illustrates a scenario to depict a processing pipeline for derivation of a first global region boundary for boundary localization of an abdominal organ of a subject, in accordance with an embodiment of the disclosure. The abdominal organ may be liver and test images for liver may be received from the surgical image-capture device 104 during surgery, for example, during hepatectomy. FIG. 3A is explained in conjunction with elements from FIG. 1 and FIG. 2. In FIG. 3A, there is shown an exemplary scenario 300A for different operations 302, 306, 308, 310, 312, and 314 in the processing pipeline.

At 302, a test video frame may be captured by the surgical image-capture device 104. The test video frame may depict (portions or entirety of) tools 302A (for example, needles) used during the surgery, blood spots 302B in different portions of the body, and an abdominal organ 302C or a portion of different abdominal organs of the human subject 110. One of the abdominal organs, i.e., the liver has to be localized by generation of a boundary in the test video frame. The view of the body in the test video frame may include portions (or in entirety) of various anatomical structures, blood spots, tumors, surgery tools, and the like.

The surgical image-capture device 104 may be configured to capture a sequence of video frames (e.g., a video). The captured sequence of video frames may depict one or more internal organs of the human subject 110. In accordance with an embodiment, the I/O device 208 may be configured to receive the captured sequence of video frames from the surgical image-capture device 104. As the captured sequence of video frames may include different internal organs of the human subject 110, certain images may be selected from the captured sequence of video frames for further processing to avoid selection of unwanted image frames, where a view of the liver may not be present or a quality score of the view may be less than a threshold quality as a result of presence of other anatomical portions of the human subject 110. The organ boundary localization circuit 202 may be configured to select the test video frame from the received sequence of video frames. The selection of the test video frame may be done based on an area occupied by the liver in the test video frame. The test video frame may be further selected when the area occupied by the liver in the test video frame is greater than a threshold area.

At 304, an appearance likelihood result is shown. The appearance likelihood result may include different intensities of pixel values 304A to 304D. The processor 202A may utilize the internal organ boundary localizer 202B to receive a plurality of training images from the medical data server 106. The plurality of training images from the dataset may include patches extracted from multi-modal images, for example, images taken from Magnetic Resonance Imaging (MRI), Computational Tomography (CT), Positron Emission Tomography (PET), Fluid Attenuated Inversion Recovery (FLAIR), and Magnetic Resonance Angiography (MRA)-based medical imaging techniques for the same or a different human subject. The processor 202A may utilize the internal organ boundary localizer 202B to compute the appearance likelihood of the abdominal organ in the test video frame. The computation of the appearance likelihood may be done based on the test video frame and the training images of the abdominal organ. The appearance likelihood result may be computed further based on a color likelihood and a texture likelihood of the liver in the test video frame. The color likelihood and the texture likelihood of the liver may be computed independent of each other. Therefore, the appearance likelihood result may be done based on prior information of how the liver looks like in terms of color and texture.

The processor 202A may utilize the internal organ boundary localizer 202B to compute a color likelihood of the liver in the test video frame. The computation of the color likelihood of the liver in the test video frame may be done based on a comparison of a color component of the test video frame with a color component in the training images for different portions of the liver. The color component may correspond to an RGB color model. The processor 202A may utilize the internal organ boundary localizer 202B to compute a texture likelihood of the liver in the test video frame. The computation of the texture likelihood of the liver in the test video frame may be done based on a comparison of a texture component of the test video frame with a texture component in the training images corresponding to the liver. The color likelihood and the texture likelihood may be computed independent of each other to compute the appearance likelihood result (as shown at 304) of the abdominal organ in the test video frame.

At 306, the global segmentation result is shown. The global segmentation result may depict different tools 306A and 306B used during the surgery, blood spots 306C, and (portions or entirety) of abdominal organs 302D and 302E in the test video frame. The global segmentation result may include a view of various anatomical portions, blood spots, tumors, tools, and the like. The global segmentation result may be represented as a plurality of regions in the test video frame. The processor 202A may utilize the internal organ boundary localizer 202B to globally segment the test video frame to a plurality of regions and obtain the global segmentation result based on the plurality of regions. The segmentation may serve as a first to localize organ boundary in the test video frame and may facilitate segregation of the test video frame into different regions that exhibits different pixel information.

In accordance with an embodiment, the processor 202A may utilize the internal organ boundary localizer 202B to assign a different color to each of the plurality of regions. The global segmentation result may be generated by the global segmentation of the test video frame. Global segmentation of the test video frame may be done based on partitions of the test video frame into the plurality of parts or the plurality of regions, by grouping pixels that have similar characteristics into one region. Different methods used for global segmentation may include thresholding, line detection, canny edge detection, and the like.

At 308, a global edge detection result is shown. The global edge detection result may depict detected edges 308A and 308B in the test video frame. The processor 202A may utilize the internal organ boundary localizer 202B to detect edges of the plurality of regions. The global edge detection result may be generated by the detection of the edges of the plurality of regions. Detection of edges may be one of the operations for localization of the organ boundary. The global edge detection result may be utilized to locate the pixels in the segmented result that corresponds to the edges of different image features, such as the abdominal organs, tools, and blood spots present in the test video frame. The global edge detection result may usually be done with a first and/or second derivative measurement that may be followed by a test that marks the pixel to an edge of the abdominal organ. The global edge detection result may include a binary image that may contain only the detected edge pixels.

At 310, an integrated image is shown. The integrated image may include a plurality of new regions 310A to 310D. In accordance with an embodiment, the processor 202A may utilize the internal organ boundary localizer 202B to merge the plurality of regions identified in the global segmentation result. The plurality of regions may be merged based on the computed appearance likelihood result, the global segmentation result, and the global edge detection result that corresponds to the test video frame. The computed appearance likelihood result, the global segmentation result, and the global edge detection result may be integrated to obtain the integrated image. The plurality of regions in the global segmentation result may be merged together or retained as separate regions based on both of the appearance likelihood result and the global edge detection result. In an exemplary scenario, when two regions from the plurality of regions have very low probability for localization of the liver in a probability map for the liver, the two regions may be retained as separated regions.

Four regions 306D to 306G may be integrated into one region when the four regions 306D to 306G exhibit a high probability for localization of liver in a probability map for the liver. Also, the four regions 306D to 306G may be integrated to a single region in accordance with the value information of the detected edges from the global edge detection result. The four regions 306D to 306G in the global segmentation result may be merged into a single region 310A in the integrated image. The merged region 310A may be assigned a new color. The two regions 306H and 306J in the global segmentation result may be merged into a single region 310B in the integrated image based on the appearance likelihood result and the global edge detection result. The merged region 310B may be assigned another new color. The region 306I may remain separated from adjacent regions in the global segmentation result.

The region 310C in the integrated image may correspond to the region 306I in the global segmentation result. The plurality of regions apart from the abdominal regions that have not been labelled for the sake of brevity in the global segmentation result may be merged into the region 310D in the integrated image. The merged region 310D may be assigned a new color that may be different from the colors assigned to the regions 310A to 310C. Segmentation boundary may be achieved for the plurality of regions in the integrated image.

At 312, a recolored image for the plurality of regions is shown. The regions 312A to 312D is in the recolored image. The regions 312A to 312D in the recolored image may correspond to the regions 310A to 310D respectively in the integrated image. The processor 202A may utilize the internal organ boundary localizer 202B to recolor the plurality of regions in the integrated image of the test video frame with four or five colors to maximize contrast between adjacent regions of the plurality of regions and obtain distinct edges in the global edge detection result. The regions 310A to 310D in the integrated image may be recolored to the regions 312A to 312D in the recolored image respectively for enhancement of the segmentation boundary of the integrated image. All the regions in the integrated image may be recolored based on a four-color theorem. A five color theorem or the like may also be used for enhancement of the segmentation boundary of the integrated image. The recolor of the integrated image may help in another edge detection apart from the detected edges in the first global edge detection result. The recolor of the integrated image to the recolored image may increase the contrast of a boundary in the global edge detection result.

At 314, a first global region boundary for localization of the abdominal organ (liver) in the test video frame is shown. The first global region boundary may be represented with different colors (for example, colored regions 314A to 314C). In accordance with an embodiment, the processor 202A may utilize the internal organ boundary localizer 202B to derive the first global region boundary of the abdominal organ (the liver). After the coloration of the plurality of regions in the recolored image of the test video frame, distinct edges may be obtained in the first global region boundary image. Different contrast in the edges is shown by colored regions 314A to 314C. After coloration, the edge detection may be utilized to identify discontinuities in brightness values that may cause a sharp change in intensity values.

Global segmentation may be further utilized to find different regions in the test video frame, based on the pixel characteristics of different regions in the test video frame. After different regions are merged in the integrated image and recolored in the recolored image, the first global region boundary may be derived at 314. The first global region boundary (at 314) may be depicted by a contour (outline) that irregularly (or discontinuously) traces a shape of the abdominal organ in the test video frame. Such contour may be further utilized to separate the abdominal organ from the background region in the test video frame. The first global region boundary (obtained at 314) may be achieved based on implementation of line fitting or edge descriptors-based techniques.

Figure 3B:
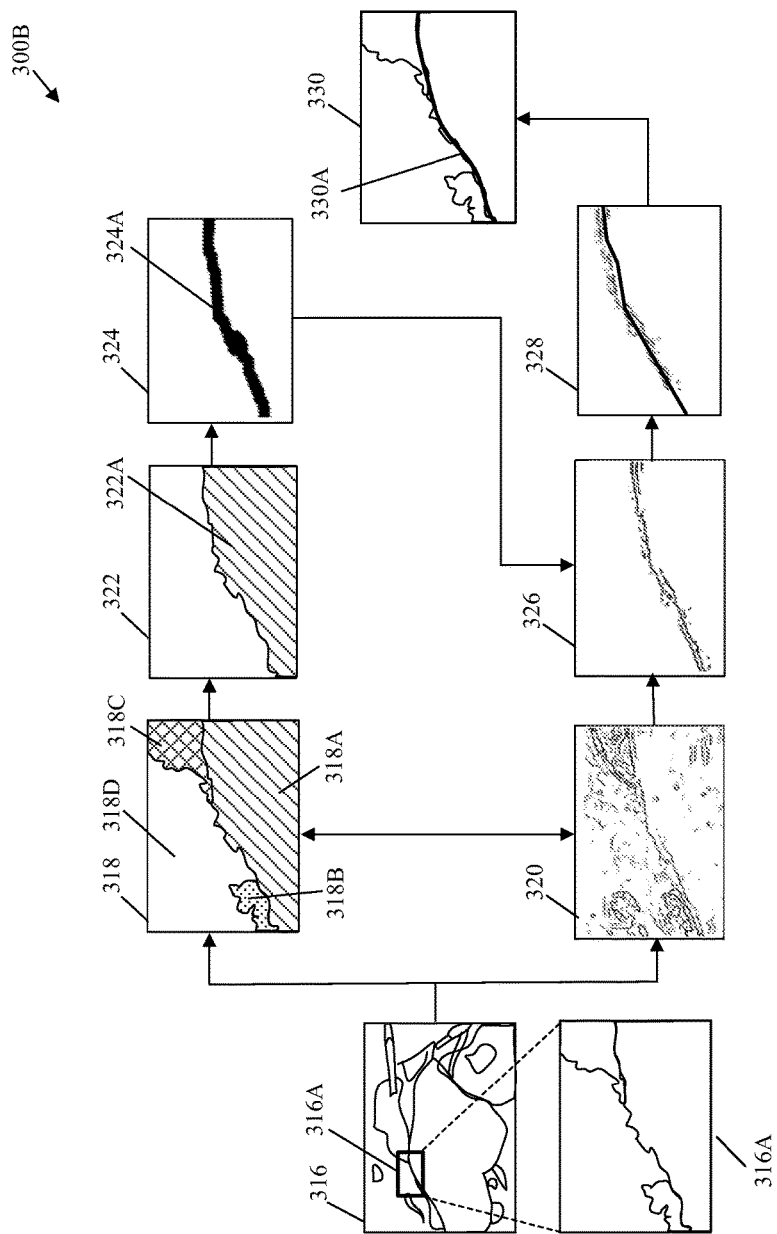
FIG. 3B illustrates an exemplary scenario for determination of a plurality of local region boundaries from a plurality of local sub regions in the selected test video frame, in accordance with an embodiment of the disclosure.

FIG. 3B illustrates an exemplary scenario for determination of a plurality of local region boundaries from a plurality of local sub regions in the selected test video frame, in accordance with an embodiment of the disclosure. Such plurality of local region boundaries may be utilized for boundary localization of an abdominal organ (for example, the liver) of a subject during surgery, e.g., hepatectomy. FIG. 3B is explained in conjunction with elements from FIGS. 1, 2, and 3A. With reference to FIG. 3B, there is shown a scenario 300B to depict a processing pipeline for determination of a plurality of local region boundaries from a plurality of local sub regions in the selected test video frame. In FIG. 3B, there is shown different operations 316 to 330 in the processing pipeline that may be executed along with the operations 302 to 314 described in FIG. 3A.

At 316, a local window may move around different regions in the test video frame to select a local sub region 316A from the test video frame. The local sub region 316A may be selected by a local window with guidance from the derived first global region boundary (estimated at 314 in FIG. 3A) of the abdominal organ. In accordance with an embodiment, the processor 202A mag utilize the internal organ boundary localizer 202B to select the plurality of local sub regions to determine a plurality of local boundaries based on the generated first global region boundary of the abdominal organ. The determination of the plurality of local region boundaries may require selection of a plurality of local windows.

At 318, the local segmentation result is shown with different regions 318A to 318D in the local segmentation result. In accordance with an embodiment, the processor 202A may utilize the internal organ boundary localizer 202B to locally segment the local sub region 316A of the abdominal organ in the selected test video frame. The local segmentation may be executed on the local sub region 316A to produce different regions 318A to 318D. The local segmentation result may provide a rough estimate of the localization of boundary of the abdominal organ. The local segmentation may be done by a suitable image segmentation technique that may be known to one skilled in the art.

At 320, the local edge detection result is shown. The processor 202A may utilize the internal organ boundary localizer 202B to generate edges of the local sub region 316A from the local segmentation result. The local edge detection result may be derived based on the generated edges of the plurality of local sub regions 316A from the local segmentation result. The generated edges may still come from the local segmentation of the local sub region 316A of the abdominal organ that may be rough and coarse. However, the local segmentation may facilitate maximization of consistency between region boundary from the local segmentation result and the generated edges from the local edge detection result. In accordance with an embodiment, the generated edges of the local sub region 316A may include a first type of edges and a second type of edges. The local edge detection result may show a lot of edges that may comprise the first type of edges and the second type of edges. The first type of edges may correspond to strong edges and the second type of edges may correspond to weak edges.

At 322, the region of interest from the derived first global region boundary (at 314) is shown. The region of interest may be labelled with 322A. The global region boundary has been derived at 314 in FIG. 3A. The region of interest 322A may be obtained by comparison of the local segmentation result and the global region boundary from FIG. 3A. The regions 318B and 318C of the local segmentation result may be eliminated (at 322) based on the global region boundary (obtained at 314 of FIG. 3A). The regions 318B and 318C may not be associated with the abdominal organ present in the test video frame and therefore, the regions 318A and 318B may be eliminated. The region of interest 322A may correspond to the region 318A of the local segmentation result. The region of interest 322A may be the region of interest associated with the abdominal organ (the liver) depicted in the test video frame.

At 324, the edge dilation of the local sub region 316A is shown. The dilated edge may be labelled as 324A. In accordance with an embodiment, the processor 202A may utilize the internal organ boundary localizer 202B to dilate the generated edges of the local sub region, based on the first global region boundary of the abdominal organ and the local segmentation result. The edge dilation may add pixels to the boundaries of the region of interest 322A (obtained at 322). A number of pixels added or removed from the region of interest 322A may depend on a size and a shape of a structuring element used to process the region of interest 322A.

At 326, the masking of the generated edges is shown. The processor 202A may utilize the internal organ boundary localizer 202B to retain the first type of edges from the generated edges of the local sub region 316A of the abdominal organ (the liver), based on a masking operation on the second type of edges using the dilated edges. The first type of edges may correspond to strong edges and the second type of edges may correspond to the weak edges. With the masking operation, the weak edges may be removed and the strong edges may be retained. However, the strong edges may include discontinuous edges as shown in the edge detection result. The edge dilation and the local edge detection result be utilized to execute the masking operation. In some cases, the masking operation may further remove some portion of dilation from the dilated edge 324A. An indicator function may be utilized in the masking operation to indicate the location of the abdominal organ (the liver). The value of "1" for the indicator function may indicate a presence of the abdominal organ (the liver) and a "0" may indicate an absence of the abdominal organ (the liver). The edges shown in the masking operation may be taken as a point set in 2-D space and a single color space fitting may be done. The remaining part within the mask may be interpolated to get a single curve in next of interpolation.

At 328, the interpolation of the edges retained after the masking operation is shown by a single curve 328A. The processor 202A may utilize the internal organ boundary localizer 202B to interpolate the retained first type of edges of the local sub region 316A of the plurality of local sub regions of the abdominal organ (the liver) by the single curve 328A. The interpolation may be done on the strong edges and may result in the single curve 328A that may correspond to the edge of the abdominal organ.

At 330, the local region boundary associated with a single color space fitting boundary 330A is shown. In accordance with an embodiment, the processor 202A may utilize the internal organ boundary localizer 202B to generate a single color space fitting boundary 330A on the interpolated single curve 328A for the local sub region 316A. The local boundaries may be determined from the generated single color space fitting boundary for the local sub region 316A of the test video frame.

Figure 3C:
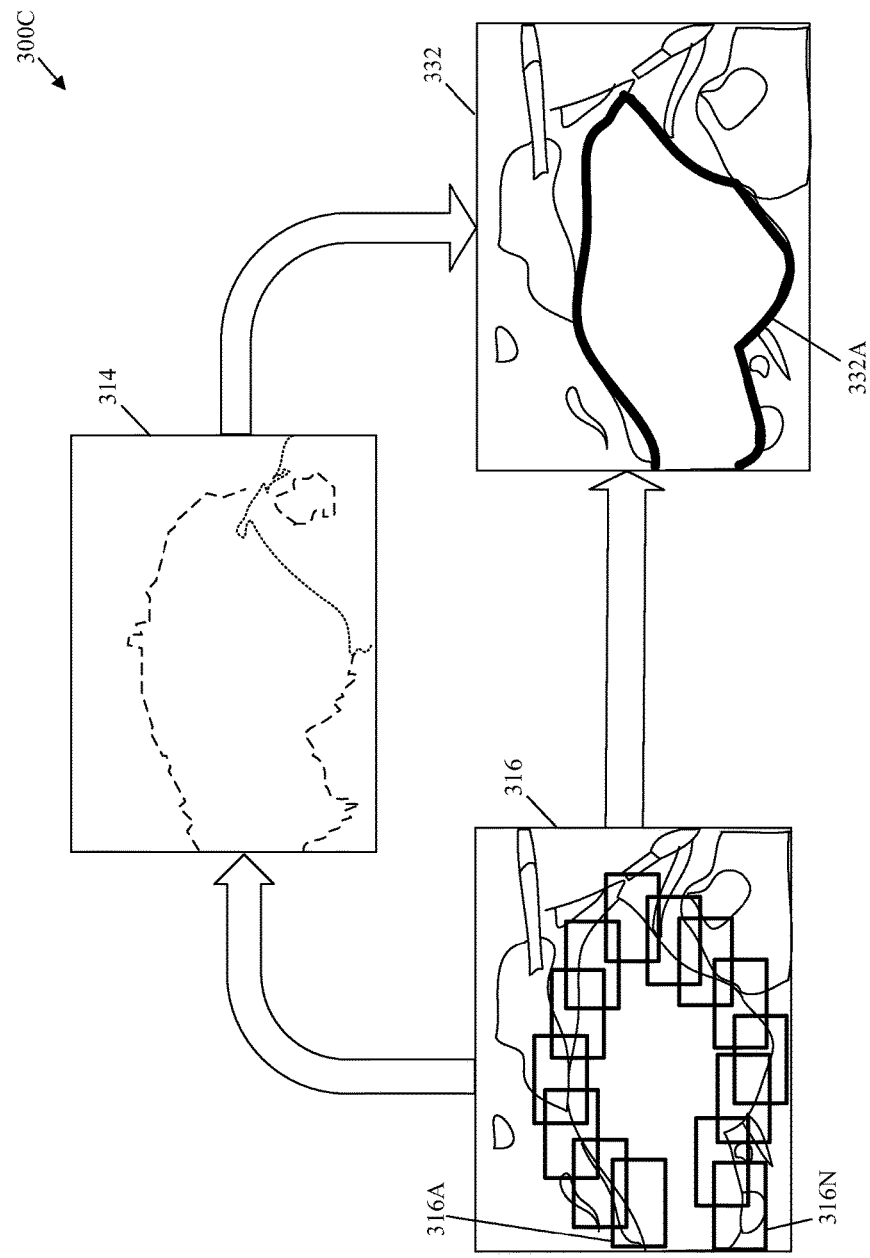
FIG. 3C illustrates an exemplary scenario for boundary localization in the selected test video frame for an abdominal organ of a subject, in accordance with an embodiment of the disclosure.

FIG. 3C illustrates an exemplary scenario for boundary localization in the selected test video frame for an abdominal organ of a subject, in accordance with an embodiment of the disclosure. FIG. 3C is explained in conjunction with elements from FIGS. 1, 2, 3A and 3B. With reference to FIG. 3C, there is shown a scenario 300C for boundary localization in a selected test video frame at 332.

At 316, the selected test image frame with a plurality of local windows to select local sub regions 316A to 316N is shown. The test video frame is shown with a plurality of local windows to select local sub regions 316A to 316N. In accordance with an embodiment, the processor 202A may utilize the internal organ boundary localizer 202B to determine a plurality of local region boundaries for the plurality of local sub regions 316A to 316N of the abdominal organ (the liver) in the selected test video frame. Such determination may be done, based on a local segmentation result and a local edge detection result (as discussed in FIG. 3B) of each of the plurality of local sub regions 316A to 316N of the abdominal organ (the liver). The first global region boundary (obtained at 314) is shown in detail in FIG. 3A. The plurality of local region boundaries 316A to 316N for the abdominal organ in the test video frame may be determined with guidance from the derived first global region boundary (at 314) of the abdominal organ (the liver).

At 332, the processor 202A may utilize the internal organ boundary localizer 202B to generate a second global region boundary 332A, based on the determined plurality of local region boundaries and the first global region boundary, for the abdominal organ in the test video frame of the captured sequence of video frames. In accordance with an embodiment, the processor 202A may utilize the internal organ boundary localizer 202B to localize the abdominal organ (the liver) within the body of the subject in the surgery, based on the generated second global region boundary for the abdominal organ (the liver). In accordance with an embodiment, the processor 202A may utilize the internal organ boundary localizer 202B to overlap the generated second global region boundary 332A for the abdominal organ (the liver) at a contour of the localized abdominal organ (the liver) in the test video frame and different test video frames that are a part of the captured sequence of video frames received as a continuous video feed from the surgical image-capture device 104.

In accordance with an embodiment, the processor 202A may utilize the internal organ boundary localizer 202B to register modified intra-operative images for the abdominal organ (the liver) with pre-operative imaging data obtained from a mode different from the surgical image-capture device 104. The modified intra-operative images may correspond to the generated second global region boundary 332A overlapped on the localized abdominal organ in the test video frame and subsequent test video frames that are a part of the captured sequence of video frames received as a continuous video feed.

In accordance with an embodiment, the processor 202A may utilize the internal organ boundary localizer 202B to generate instructions to enable navigation of the surgical image-capture device 104 and a surgical instrument within the body of the subject to reach to the localized abdominal organ (the liver) for a precision image-guided surgery of the localized abdominal organ (the liver). Local sub regions may be more homogeneous than global variations in the test video frame. Local sub regions may be less affected by global variations in the test video frame. A local localization by boundary generation may be computed with a maximum consistency between the local segmentation result and the local edge detection result.

For image processing, segmentation and edge detection are two different processes that complement each other. The segmentation may depict less accurate localization of the boundary in an image. In contrast, the edge detection may depict more accurate localization but with some false positives. The segmentation may give a rough estimate of the localization of organ boundary and the local segmentation may determine exactly where the boundary is present. Therefore, the global process may provide a range in which the boundary of the internal organ may be present and the local process may provide with the localization of the organ boundary.

Figure 4A:
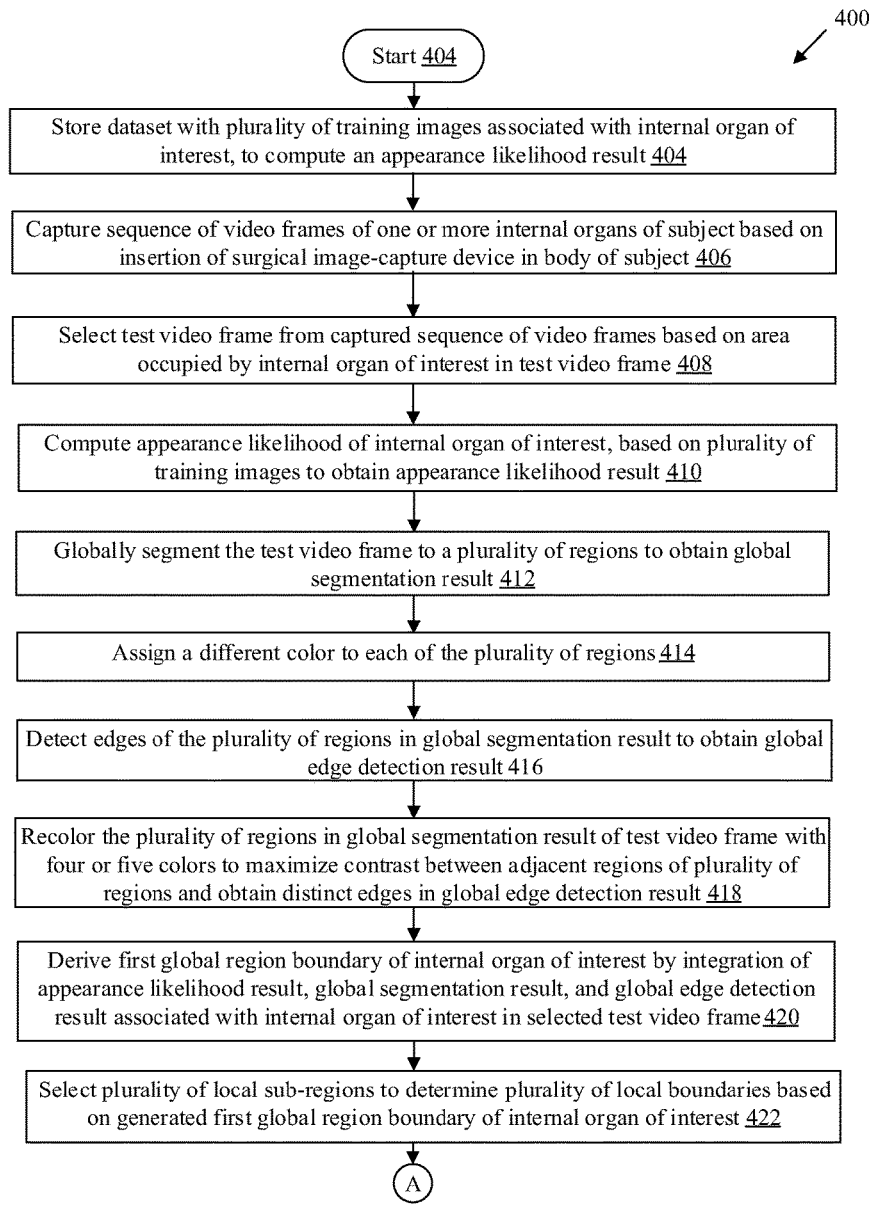
FIG. 4A, FIG. 4B, and FIG. 4C, collectively, illustrate a flow chart that depicts exemplary operations for boundary localization of an internal organ of a subject for providing assistance in a surgery, in accordance with an embodiment of the disclosure.
Figure 4B:
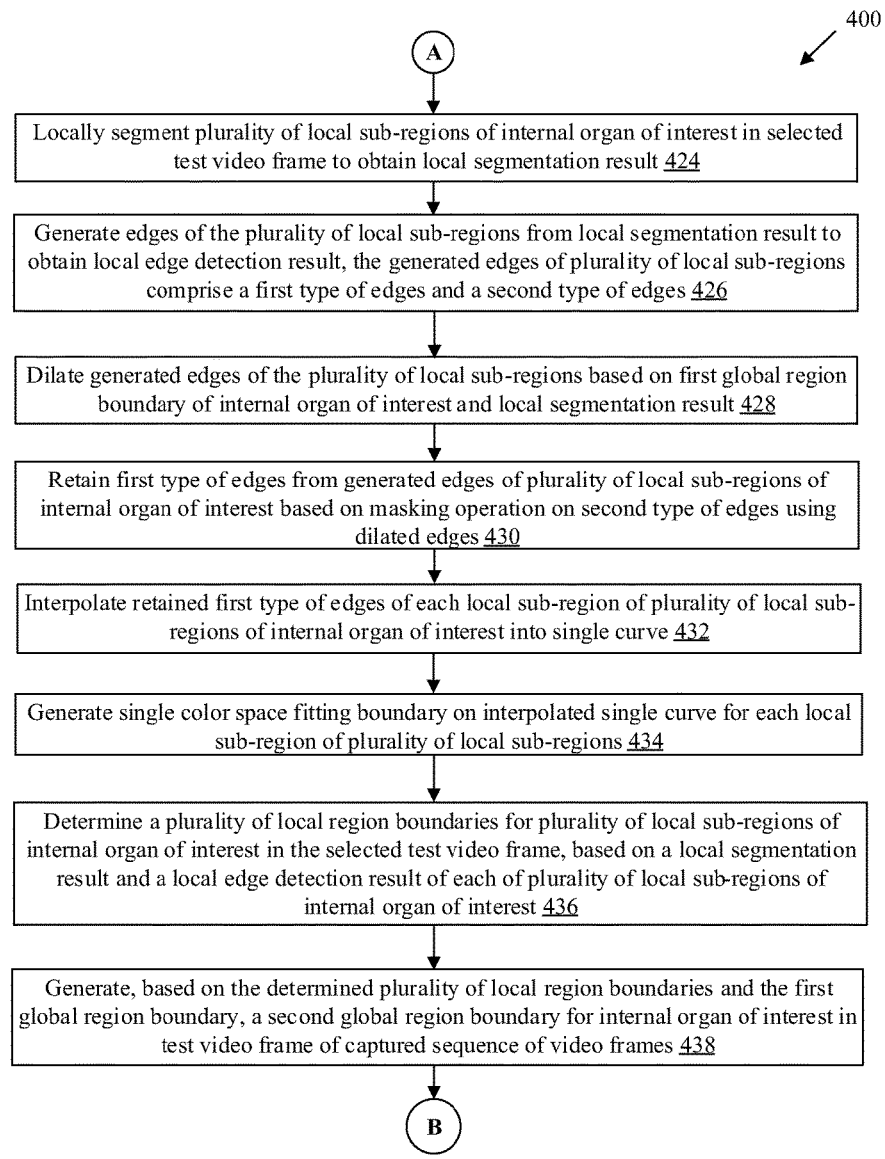
Figure 4C:
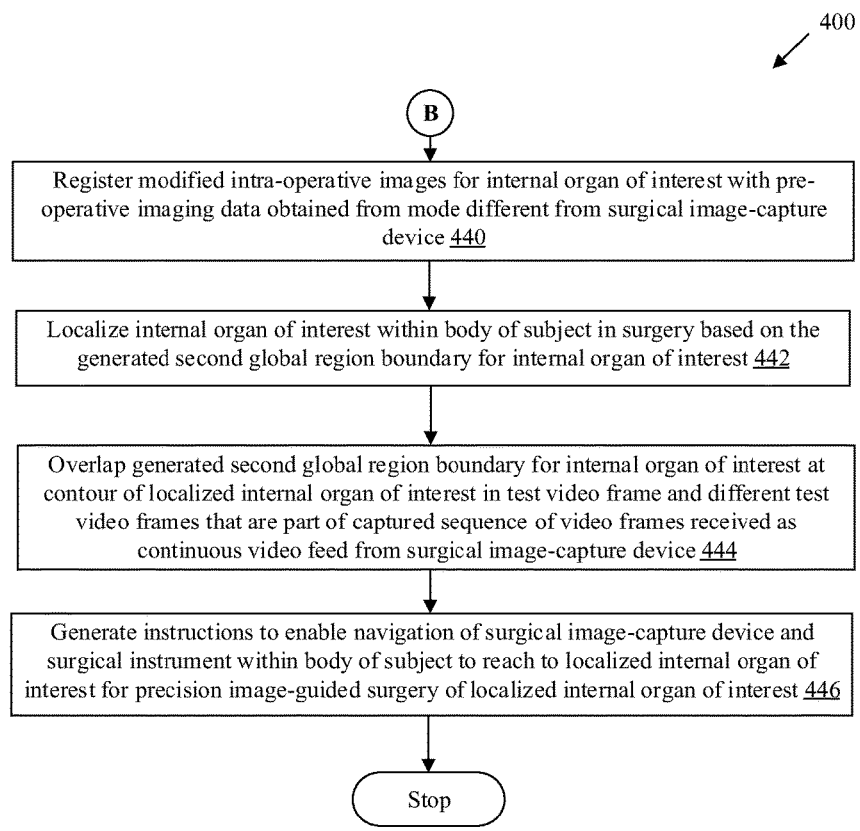

FIGS. 4A, 4B, and 4C, collectively, illustrate a flow chart that depicts exemplary operations for boundary localization of an internal organ of a subject for providing assistance in a surgery, in accordance with an embodiment of the disclosure. With reference to FIGS. 4A, 4B, and 4C, there is shown a flowchart 400. The flowchart 400 is described in conjunction with elements from FIGS. 1, 2, and 3A to 3C. The method, in accordance with the flowchart 400, may be implemented in the surgical assistive device 102. The method starts at 402 and proceeds to 404.

At 404, a dataset with a plurality of training images associated with an internal organ of interest 112 may be stored to compute an appearance likelihood result. The memory 204 may be configured to store a dataset with a plurality of training images associated with an internal organ of interest 112, to compute an appearance likelihood result for the internal organ of interest 112.

At 406, a sequence of video frames of one or more internal organs of a subject may be captured, based on insertion of the surgical image-capture device 104 in a body of the human subject 110. The surgical image-capture device 104 may be configured to capture a sequence of video frames of one or more internal organs of a subject, based on insertion of the surgical image-capture device 104 in the body of the human subject 110.

At 408, a test video frame from the captured sequence of video frames may be selected, based on an area occupied by the internal organ of interest 112 in the test video frame. The area occupied by the internal organ of interest 112 in the test video frame may be greater than a threshold area. The processor 202A may be configured to select a test video frame from the captured sequence of video frames, based on an area occupied by the internal organ of interest 112 in the test video frame.

At 410, an appearance likelihood of the internal organ of interest 112 may be computed, based on the plurality of training images to obtain the appearance likelihood result. The processor 202A may be configured to compute an appearance likelihood of the internal organ of interest 112, based on the plurality of training images to obtain the appearance likelihood result.

At 412, the test video frame may be globally segmented to a plurality of regions to obtain a global segmentation result. The processor 202A may utilize the internal organ boundary localizer 202B to globally segment the test video frame to a plurality of regions to obtain a global segmentation result.

At 414, a different color may be assigned to each of the plurality of regions of the global segmentation result. The processor 202A may utilize the internal organ boundary localizer 202B to assign a different color to each of the plurality of regions of the global segmentation result.

At 416, edges of the plurality of regions may be detected in the global segmentation result to obtain a global edge detection result. The processor 202A may utilize the internal organ boundary localizer 202B to detect edges of the plurality of regions in the global segmentation result to obtain a global edge detection result.

At 418, the plurality of regions of the global segmentation result of the test video frame may be recolored with four or five colors to maximize contrast between adjacent regions of plurality of regions and obtain distinct edges in global edge detection result. The processor 202A may utilize the internal organ boundary localizer 202B to recolor the plurality of regions of the global segmentation result of the test video frame with four or five colors to maximize contrast between adjacent regions of plurality of regions and obtain distinct edges in global edge detection result.

At 420, a first global region boundary of the internal organ of interest 112 may be derived, by integration of the appearance likelihood result, the global segmentation result, and the global edge detection result associated with the internal organ of interest 112 in selected test video frame. The processor 202A may utilize the internal organ boundary localizer 202B to derive a first global region boundary of the internal organ of interest 112, by integration of the appearance likelihood result, the global segmentation result, and the global edge detection result associated with the internal organ of interest 112 in selected test video frame.

At 422, a plurality of local sub regions may be selected to determine plurality of local boundaries based on generated first global region boundary of internal organ of interest 112. The processor 202A may utilize the internal organ boundary localizer 202B to select a plurality of local sub regions to determine a plurality of local boundaries based on the generated first global region boundary of the internal organ of interest 112.

At 424, the plurality of local sub regions of internal organ of interest 112 in selected test video frame may be locally segmented to obtain a local segmentation result. The processor 202A may utilize the internal organ boundary localizer 202B to locally segment the plurality of local sub regions of internal organ of interest 112 in selected test video frame to obtain a local segmentation result.

At 426, edges of the plurality of local sub regions may be generated from the local segmentation result to obtain a local edge detection result. The generated edges of plurality of local sub regions may comprise a first type of edges and a second type of edges. The processor 202A may utilize the internal organ boundary localizer 202B to generate edges for the plurality of local sub regions from the local segmentation result to obtain a local edge detection result.

At 428, the generated edges of the plurality of local sub regions may be dilated, based on the first global region boundary of the internal organ of interest 112 and the local segmentation result. The processor 202A may utilize the internal organ boundary localizer 202B to dilate the generated edges of the plurality of local sub regions, based on the first global region boundary of the internal organ of interest 112 and the local segmentation result.

At 430, the first type of edges may be retained from the generated edges of the plurality of the local sub regions of the internal organ of interest 112, based on a masking operation on the second type of edges using dilated edges. The processor 202A may utilize the internal organ boundary localizer 202B to retain the first type of edges from the generated edges of the plurality of the local sub regions of the internal organ of interest 112, based on a masking operation on the second type of edges using dilated edges.

At 432, the retained first type of edges of each local sub region of the plurality of local sub regions of the internal organ of interest 112 may be interpolated into a single curve. The processor 202A may utilize the internal organ boundary localizer 202B to interpolate the retained first type of edges of each local sub region of the plurality of local sub regions of the internal organ of interest 112 into a single curve.

At 434, the single color space fitting boundary may be generated on the interpolated single curve for each local sub region of the plurality of local sub regions. The processor 202A may utilize the internal organ boundary localizer 202B to generate the single color space fitting boundary on the interpolated single curve for each local sub region of the plurality of local sub regions.

At 436, a plurality of local region boundaries may be determined for the plurality of local sub regions of the internal organ of interest 112 in the selected test video frame, based on the local segmentation result and the local edge detection result of each of plurality of local sub regions of internal organ of interest 112. The processor 202A may utilize the internal organ boundary localizer 202B to determine a plurality of local region boundaries for the plurality of local sub regions of the internal organ of interest 112 in the selected test video frame, based on the local segmentation result and the local edge detection result of each of plurality of local sub regions of the internal organ of interest 112.

At 438, a second global region boundary may be generated for internal organ of interest 112 in test video frame of captured sequence of video frames, based on the determined plurality of local region boundaries and the first global region boundary. The processor 202A may utilize the internal organ boundary localizer 202B to generate a second global region boundary for the internal organ of interest 112 in test video frame of captured sequence of video frames, based on the determined plurality of local region boundaries and the first global region boundary.

At 440, a modified intra-operative images for internal organ of interest 112 may be registered with pre-operative imaging data obtained from mode different from surgical image-capture device 104. The modified intra-operative images may correspond to the generated second global region boundary overlapped on localized internal organ of interest 112 in the test video frame and subsequent test video frames that are part of the captured sequence of video frames received as continuous video feed. The organ boundary localization circuit 202 may be configured to register a modified intra-operative images for internal organ of interest 112 with pre-operative imaging data obtained from mode different from surgical image-capture device 104.

At 442, the internal organ of interest 112 may be localized within a body of human subject 110 during surgery based on the generated second global region boundary for internal organ of interest 112. The organ boundary localization circuit 202 may be configured to localize the internal organ of interest 112 within a body of human subject 110 during surgery based on the generated second global region boundary for internal organ of interest 112.

At 444, the generated second global region boundary for internal organ of interest 112 may be overlapped at contour of the localized internal organ of interest 112 in the test video frame and different test video frames that may be part of captured sequence of video frames received as continuous video feed from surgical image-capture device 104. The organ boundary localization circuit 202 may be configured to overlap the generated second global region boundary for internal organ of interest 112 at a contour of the localized internal organ of interest 112 in the test video frame and different test video frames that may be part of captured sequence of video frames received as continuous video feed from surgical image-capture device 104.

At 446, instructions may be generated to enable navigation of the surgical image-capture device 104 and the surgical instrument within body of human subject 110 to reach to the localized internal organ of interest 112 for precision image-guided surgery of localized internal organ of interest 112. The processor 202A may be configured to generate instructions to enable navigation of the surgical image-capture device 104 and the surgical instrument within body of human subject 110 to reach to the localized internal organ of interest 112 for precision image-guided surgery of localized internal organ of interest 112. Control passes to end.

In accordance with an embodiment of the disclosure, the surgical assistive device 102 for boundary localization of an internal organ of a subject for providing assistance during surgery may comprise the surgical assistive device 102 (FIG. 1). The surgical assistive device 102 may comprise one or more circuits, such as the organ boundary localization circuit 202 (FIG. 2). The organ boundary localization circuit 202 may be configured to select a test video frame from the captured sequence of video frames. The organ boundary localization circuit 202 may be further configured to derive a first global region boundary of an internal organ of interest by integration of an appearance likelihood result, a global segmentation result, and a global edge detection result associated with the internal organ of interest in the selected test video frame. The organ boundary localization circuit 202 may be further configured to determine a plurality of local region boundaries for a plurality of local sub regions of the internal organ of interest in the selected test video frame. The local region boundaries may be determined based on a local segmentation result and a local edge detection result of each of the plurality of local sub regions of the internal organ of interest. The plurality of local region boundaries may be determined with guidance from the derived first global region boundary of the internal organ of interest. The organ boundary localization circuit 202 may be further configured to generate, based on the determined plurality of local region boundaries and the first global region boundary, a second global region boundary for the internal organ of interest in the test video frame of the captured sequence of video frames. The organ boundary localization circuit 202 may be configured to localize the internal organ of interest within the body of the subject in the surgery, based on the generated second global region boundary for the internal organ of interest. In accordance with an embodiment, the internal organ of interest is an abdominal organ.

In accordance with an embodiment, the organ boundary localization circuit may be further configured to receive the captured sequence of video frames of the one or more internal organs of the subject from the surgical image-capture device 104. In accordance with an embodiment, the test video frame may be selected from the captured sequence of video frames based on an area occupied by the internal organ of interest in the test video frame. In accordance with an embodiment, the area occupied by the internal organ of interest in the test video frame may be greater than a threshold area.

In accordance with an embodiment, the organ boundary localization circuit may be further configured to receive a plurality of training images of the internal organ of interest from a medical data server. In accordance with an embodiment, the organ boundary localization circuit may be further configured to compute an appearance likelihood of the internal organ of interest, based on the plurality of training images, the appearance likelihood result may be generated by the computation of the appearance likelihood.

In accordance with an embodiment, the organ boundary localization circuit may be further configured to globally segment the test video frame to a plurality of regions to obtain the global segmentation result. In accordance with an embodiment, the organ boundary localization circuit may be further configured to assign a different color to each of the plurality of regions. In accordance with an embodiment, the global segmentation result may be generated by the global segmentation of the test video frame.

In accordance with an embodiment, the organ boundary localization circuit may be further configured to detect edges of the plurality of regions in the global segmentation result. In accordance with an embodiment, the global edge detection result may be generated by the detection of the edges of the plurality of regions.

In accordance with an embodiment, the organ boundary localization circuit may be further configured to recolor the plurality of regions in the global segmentation result of the test video frame with four or five colors to maximize contrast between adjacent regions of the plurality of regions and obtain distinct edges in the global edge detection result.

In accordance with an embodiment, the organ boundary localization circuit may be further configured to select the plurality of local sub regions to determine the plurality of local boundaries based on the generated first global region boundary of the internal organ of interest. In accordance with an embodiment, the organ boundary localization circuit may be further configured to locally segment the plurality of local sub regions of the internal organ of interest in the selected test video frame. In accordance with an embodiment, the local segmentation result may be generated by the local segmentation of the plurality of local sub regions of the internal organ of interest. In accordance with an embodiment, the organ boundary localization circuit may be further configured to generate edges of the plurality of local sub regions from the local segmentation result. In accordance with an embodiment, the local edge detection result may be derived by the generated edges of the plurality of local sub regions from the local segmentation result.

In accordance with an embodiment, the organ boundary localization circuit may be further configured to dilate the generated edges of the plurality of local sub regions based on the first global region boundary of the internal organ of interest and the local segmentation result. In accordance with an embodiment, the generated edges of the plurality of local sub regions may comprise a first type of edges and a second type of edges. In accordance with an embodiment, the organ boundary localization circuit may be further configured to retain the first type of edges from the generated edges of the plurality of local sub regions of the internal organ of interest based on a masking operation on the second type of edges using the dilated edges.

In accordance with an embodiment, the organ boundary localization circuit may be further configured to interpolate the retained first type of edges of each local sub region of the plurality of local sub regions of the internal organ of interest into a single curve. In accordance with an embodiment, the organ boundary localization circuit may be further configured to generate a single color space fitting boundary on the interpolated single curve for each local sub region of the plurality of local sub regions. In accordance with an embodiment, the plurality of local boundaries may be determined from the generated single color space fitting boundary for each local sub region of the plurality of local sub regions in the test video frame.

In accordance with an embodiment, the organ boundary localization circuit may be further configured to overlap the generated second global region boundary for the internal organ of interest at a contour of the localized internal organ of interest in the test video frame and different test video frames that are a part of the captured sequence of video frames received as a continuous video feed from the surgical image-capture device. In accordance with an embodiment, the organ boundary localization circuit may be further configured to register modified intra-operative images for the internal organ of interest with pre-operative imaging data obtained from a mode different from the surgical image-capture device. In accordance with an embodiment, the modified intra-operative images may correspond to the generated second global region boundary overlapped on the localized internal organ of interest in the test video frame and subsequent test video frames that are a part of the captured sequence of video frames received as a continuous video feed.

In accordance with an embodiment, the organ boundary localization circuit may be further configured to generate instructions to enable navigation of the surgical image-capture device and a surgical instrument within the body of the subject to reach to the localized internal organ of interest for a precision image-guided surgery of the localized internal organ of interest.

Various embodiments of the disclosure may provide a non-transitory computer readable medium and/or storage medium, and/or a non-transitory machine readable medium and/or storage medium with a machine code and/or a set of instructions stored thereon and executable by a machine and/or a computer to provide assistance in a surgery. The set of instructions in the surgical assistive device 102 may cause the machine and/or computer to perform the steps that comprise reception of the plurality of training images of the internal organ of interest from the medical data server 106 (FIG. 1). A sequence of video frames of one or more internal organs of subject may be captured based on insertion of surgical image-capture device in a body of subject. A first global region boundary of an internal organ of interest may be derived by integration of an appearance likelihood result, a global segmentation result, and a global edge detection result associated with the internal organ of interest in the selected test video frame. A plurality of local region boundaries may be determined for a plurality of local sub regions of the internal organ of interest in the selected test video frame, based on a local segmentation result and a local edge detection result of each of the plurality of local sub regions of the internal organ of interest. Based on the determined plurality of local region boundaries and the first global region boundary, a second global region boundary for the internal organ of interest may be generated in the test video frame of the captured sequence of video frames. The internal organ of interest may be localized within the body of the subject in the surgery, based on the generated second global region boundary for the internal organ of interest.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system that has an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that falls within the scope of the appended claims.

What is claimed is:

1. A surgical assistive device, comprising:
   a surgical image-capture device configured to capture a sequence of video frames of one or more internal organs of a subject based on insertion of the surgical image-capture device in a body of the subject; and
   an organ boundary localization circuit configured to:
   select a test video frame from the captured sequence of video frames;
   derive a first global region boundary of an internal organ of interest by integration of an appearance likelihood result, a global segmentation result, and a global edge detection result associated with the internal organ of interest in the selected test video frame;
   determine a plurality of local region boundaries for a plurality of local sub regions of the internal organ of interest in the selected test video frame, based on a local segmentation result and a local edge detection result of each of the plurality of local sub regions of the internal organ of interest, wherein the plurality of local region boundaries are determined from the derived first global region boundary of the internal organ of interest;
   generate, based on the determined plurality of local region boundaries and the first global region boundary, a second global region boundary for the internal organ of interest in the test video frame of the captured sequence of video frames; and
   localize the internal organ of interest within the body of the subject in a surgery, based on the generated second global region boundary for the internal organ of interest.

2. The surgical assistive device according to claim 1, wherein the internal organ of interest is an abdominal organ.

3. The surgical assistive device according to claim 1, wherein the organ boundary localization circuit is further configured to receive the captured sequence of video frames of the one or more internal organs of the subject from the surgical image-capture device, wherein the test video frame is selected from the captured sequence of video frames based on an area occupied by the internal organ of interest in the test video frame, wherein the area occupied by the internal organ of interest in the test video frame is greater than a threshold area.

4. The surgical assistive device according to claim 1, wherein the organ boundary localization circuit is further configured to:
   receive a plurality of training images of the internal organ of interest from a medical data server; and
   compute an appearance likelihood of the internal organ of interest, based on the plurality of training images, wherein the appearance likelihood result is generated by the computed appearance likelihood.

5. The surgical assistive device according to claim 1, wherein the organ boundary localization circuit is further configured to:
   globally segment the test video frame to a plurality of regions to obtain the global segmentation result; and
   assign a different color to each of the plurality of regions, wherein the global segmentation result is generated by the globally segmented test video frame.

6. The surgical assistive device according to claim 5, wherein the organ boundary localization circuit is further configured to detect edges of the plurality of regions in the global segmentation result, wherein the global edge detection result is generated by the detected edges of the plurality of regions.

7. The surgical assistive device according to claim 6, wherein the organ boundary localization circuit is further configured to recolor the plurality of regions in the global segmentation result of the test video frame with four or five colors to maximize contrast between adjacent regions of the plurality of regions and obtain distinct edges in the global edge detection result.

8. The surgical assistive device according to claim 1, wherein the organ boundary localization circuit is further configured to select the plurality of local sub regions to determine the plurality of local region boundaries based on the derived first global region boundary of the internal organ of interest.

9. The surgical assistive device according to claim 1, wherein the organ boundary localization circuit is further configured to locally segment the plurality of local sub regions of the internal organ of interest in the selected test video frame, wherein the local segmentation result is generated by the locally segmented plurality of local sub regions of the internal organ of interest.

10. The surgical assistive device according to claim 1, wherein the organ boundary localization circuit is further configured to generate edges of the plurality of local sub regions from the local segmentation result, wherein the local edge detection result is derived by the generated edges of the plurality of local sub regions from the local segmentation result.

11. The surgical assistive device according to claim 10, wherein the organ boundary localization circuit is further configured to dilate the generated edges of the plurality of local sub regions based on the first global region boundary of the internal organ of interest and the local segmentation result.

12. The surgical assistive device according to claim 11, wherein the generated edges of the plurality of local sub regions comprise a first type of edges and a second type of edges.

13. The surgical assistive device according to claim 12, wherein the organ boundary localization circuit is further configured to retain the first type of edges from the generated edges of the plurality of local sub regions of the internal organ of interest based on a masking operation on the second type of edges using the dilated edges.

14. The surgical assistive device according to claim 13, wherein the organ boundary localization circuit is further configured to interpolate the retained first type of edges of each local sub region of the plurality of local sub regions of the internal organ of interest into a single curve.

15. The surgical assistive device according to claim 14, wherein the organ boundary localization circuit is further configured to generate a single color space fitting boundary on the single curve for each local sub region of the plurality of local sub regions, and wherein the plurality of local region boundaries are determined from the generated single color space fitting boundary for each local sub region of the plurality of local sub regions in the test video frame.

16. The surgical assistive device according to claim 12, wherein the organ boundary localization circuit is further configured to overlap the generated second global region boundary for the internal organ of interest at a contour of the localized internal organ of interest in the test video frame and different test video frames that are a part of the captured sequence of video frames received as a continuous video feed from the surgical image-capture device.

17. The surgical assistive device according to claim 1, wherein the organ boundary localization circuit is further configured to register modified intra-operative images for the internal organ of interest with pre-operative imaging data obtained from a mode different from the surgical image-capture device, wherein the modified intra-operative images corresponds the generated second global region boundary overlapped on the localized internal organ of interest in the test video frame and subsequent test video frames that are a part of the captured sequence of video frames received as a continuous video feed.

18. The surgical assistive device according to claim 1, wherein the organ boundary localization circuit is further configured to generate instructions to enable navigation of the surgical image-capture device and a surgical instrument within the body of the subject to reach to the localized internal organ of interest for a precision image-guided surgery of the localized internal organ of interest.

19. A surgical assistive method, comprising:
capturing, by a surgical image-capture device, a sequence of video frames of one or more internal organs of a subject based on insertion of the surgical image-capture device in a body of the subject;
selecting, by an organ boundary localization (OBL) circuit, a test video frame from the captured sequence of video frames;
deriving, by the OBL circuit, a first global region boundary of an internal organ of interest by integration of an appearance likelihood result, a global segmentation result, and a global edge detection result associated with the internal organ of interest in the selected test video frame;
determining, by the OBL circuit, a plurality of local region boundaries for a plurality of local sub regions of the internal organ of interest in the selected test video frame, based on a local segmentation result and a local edge detection result of each of the plurality of local sub regions of the internal organ of interest, wherein the plurality of local region boundaries are determined with guidance from the derived first global region boundary of the internal organ of interest;
generating, by the OBL circuit, based on the determined plurality of local region boundaries and the first global region boundary, a second global region boundary for the internal organ of interest in the test video frame of the captured sequence of video frames; and
localizing, by the OBL circuit, the internal organ of interest within the body of the subject in a surgery, based on the generated second global region boundary for the internal organ of interest.

* * * * *